United States Patent [19]

Sankey

[11] Patent Number: 5,326,904
[45] Date of Patent: Jul. 5, 1994

[54] PEROXYACID MANUFACTURE

[75] Inventor: John P. Sankey, Warrington, England

[73] Assignee: Solvay Interox Limited, Warrington, England

[21] Appl. No.: 76,179

[22] Filed: Jun. 14, 1993

Related U.S. Application Data

[62] Division of Ser. No. 773,586, Nov. 20, 1991, which is a division of PCT/GB90/00793, May 21, 1990, Pat. No. 5,220,052.

[30] Foreign Application Priority Data

May 24, 1989 [GB] United Kingdom ............... 8911057

[51] Int. Cl.$^5$ ........................................... C07C 409/16
[52] U.S. Cl. ................................................. 562/2
[58] Field of Search .................................... 562/2

[56] References Cited

U.S. PATENT DOCUMENTS

| | | |
|---|---|---|
| 2,813,896 | 11/1957 | Krim . |
| 4,119,660 | 10/1978 | Hutchins . |
| 4,233,235 | 11/1980 | Camden et al. . |
| 4,244,884 | 1/1981 | Hutchins et al. . |
| 4,314,949 | 2/1982 | Bettle, III et al. . |
| 4,634,551 | 1/1987 | Burns et al. ..................... 252/102 |
| 4,686,063 | 8/1987 | Burns ............................ 252/102 |
| 4,852,989 | 8/1989 | Burns et al. ..................... 8/107 |
| 5,268,003 | 12/1993 | Coope et al. ..................... 8/111 |
| 5,292,451 | 3/1994 | Gethöffer et al. ............. 252/186.42 |

OTHER PUBLICATIONS

J. Amer. Chem. Soc., 1955, vol. 77, pp. 4037–4041, Parker, et al., "Peroxides. II. Preparation, Characterization and Polarographic Behavior of Long-Chain Aliphatic Peracids".

J. Amer. Chem. Soc., 1957, vol. 79, pp. 1929–1931, Parker, et al., "Peroxides. IV. Aliphatic Diperacids".

Primary Examiner—José G. Dees
Assistant Examiner—Barbara S. Frazier
Attorney, Agent, or Firm—Larson and Taylor

[57] ABSTRACT

The compound 6,6'-terephthal-di(amidoperoxyhexanoic) acid is disclosed.

1 Claim, No Drawings

PEROXYACID MANUFACTURE

The present application is a division of co-pending application Ser. No. 07/773,586 filed on Nov. 20, 1991, which is International Application PCT/GB 90/00793, filed May 21, 1990, now U.S. Pat. No. 5,220,052.

The present invention relates to a process for the manufacture of organic peroxyacids, and more particularly to peroxyacids having poor solubility in aqueous media.

The detergents industry constantly seeks to improve the cleansing performance of its compositions, and in a effort to do so under low temperature washing conditions has investigated the incorporation of quite small amounts of peroxyacids. Most of the peroxyacids contemplated have been organic peroxycarboxylic acid compounds containing at least 7 carbon atoms and many of them have exhibited poor solubility in aqueous media, a feature usually shared with the corresponding carboxylic acid from which they are or could be derived.

There have been many different processes proposed for the manufacture of organic peroxyacids, including the poorly soluble ones. A number have used sulphuric acid as a main constituent of the reaction mixture. Parker et al in JACS 77:4037–41 and/or JACS 79:1929–32 suggested the drop-wise addition of concentrated hydrogen peroxide to a sulphuric acid solution of a long chain aliphatic mono or di-carboxylic acid. Hutchins, in U.S. Pat. No. 4,119,660, discloses in column 1 that there are a number of problems with the Parker process, such as rate of peracid formation and/or small particle size of peracid product and accordingly, he suggests an alternative procedure in which the hydrogen peroxide and sulphuric acid reagents are premixed, and the solid carboxylic acid is subsequently introduced therein. Hutchins asserts that the acidity of his reaction mixture is of crucial importance, being at least 69% sulphuric acid in order to attain an unexpected decrease in reaction time, compared even with an acidity of 66.5%. Virtually the same procedure had been proposed nearly 20 years earlier by Krimm in U.S. Pat. No. 2 813 896, the difference being that the exemplified amounts of sulphuric acid were numerically lower than the range identified by Hutchins. Camden in U.S. Pat No. 4 233 235 discloses a continuous process for making similar long chain aliphatic peroxyacids and asserts in column 4 that batch processes, presumably for the same products, exhibit more safety problems and produce smaller crystals. In his process, he employs balanced continuous addition of reagents to and continuous withdrawal of product a constant residence time of his reagents in the reaction mixture. Bettle in U.S. Pat. No. 4 314 949 discloses that in a preferred method of making aliphatic percarboxylic acids, particulate carboxylic acid is added to a peroxide/sulphuric acid mixture. Hutchins in a second patent, U.S. Pat. No. 4244 884, discloses a variation to the Camden continuous process, in which he recycles mother liquor separated from the product. It will be observed that in column 3, he asserts that the carboxylic acid added to the reaction mixture typically precipitates in situ, so that most of it is in the solid form. He also indicates that the inherent reaction between carboxylic acids and hydrogen peroxide can present safety problems, since it can become uncontrollable if it is not carefully controlled.

Peroxyacids are often needed in smaller quantities than justify the capital outlay inherent in a continuously operated process. Consequently, it would be desirable to devise a batch process variation that can be readily carried out so as to avoid the formation of hazardous compositions during the entire process. In the course of investigations which have lead to the instant invention, the inventors have found that there are a number of different factors which must be balanced in order to retain a viable and safe process.

A wide range of compositions containing relatively high concentrations of hydrogen peroxide and organic material, such as carboxylic acids are conventionally viewed as hazardous on account of their tendency to decompose spontaneously. Thus, too much hydrogen peroxide in solution causes safety problems. Since the solubility of the carboxylic acid is usually rather low, it means that peroxide concentration must be kept low by increase in the water and/or sulphuric acid contents. In that context, the water content of the reaction mixture needs to be kept low because it has been demonstrated by Hutchins in obtaining U.S. Pat. No. 4,119,660 that the sulphuric acid content of the reaction is of very considerable importance in achieving a fast rate of reaction and formation of a high molecular weight peroxyacid. This may be a way of saying that the reaction equation demonstrates the value of having very little water present, since the extent of formation of percarboxylic acid is the equilibrium mixture in the liquid phase is clearly affected directly by residual water content.

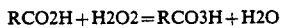

$$RCO_2H + H_2O_2 = RCO_3H + H_2O$$

However, to set against the foregoing, the inventors have also found that the solubility of the product is very dependent upon the acidity of the reaction mixture, and increases very markedly as the acidity increases. The inventors have further correlated such a finding with two other observations. Both the proportionate recovery of the product, an important factor in a batch process, and also the inherent degree of safety of operation of the process vary inversely to the acidity of the aqueous phase.

It is an object of the present invention to create a process which can be operated in batch mode in a controlled and safe fashion and from which can be recovered a crystalline peroxyacid product, preferably in high yield.

According to the present invention, there is provided a process for the manufacture of poorly-soluble aliphatic peroxyacids by reaction between an aliphatic carboxylic acid and excess hydrogen peroxide in a strongly acidic reaction medium which is characterised in that the following process sequence is employed:

1. In step 1, the aliphatic carboxylic acid is dissolved in concentrated aqueous sulphuric acid that contains no more than a maximum proportion of water which proportion varies in accordance with the solubility of the carboxylic acid from about 25% w/w water for the relatively more soluble carboxylic acids to about 10% w/w water for the relatively less soluble carboxylic acids;

2. In step 2, an equilibrium mixture of Caro's acid is made by mixing i) hydrogen peroxide, ii) sulphuric acid and iii) water said mixture containing from about 5 to 30% hydrogen peroxide, a complementary amount of sulphuric acid such that, in conjunction with the amount of sulphuric acid present in the carboxylic acid solution of step 1, the concentration of sulphuric acid in the reaction mixture at the end of step 3 is as defined therein, and the balance water, with agitation and cooling to below about 50° C., the A value, being the weight ratio of sulphuric acid to the total of water plus sulphuric acid in a composition, for the Caro's acid solution being not substantially greater than the A value of the carboxylic acid solution produced in step 1 or lower, the minimum difference between the two A values increasing as the solubility of the carboxylic acid decreases;

3. In step 3, a reaction mixture is formed by introducing the product of step 1 with agitation into a body of Caro's acid formed in step 2 and is maintained at a temperature in the range of from 0° to 50° C., the rate of introduction being controlled such that the aliphatic carboxylic acid remains substantially entirely in solution before it reacts with hydrogen peroxide or permonosulphuric acid and the introduction is stopped no later than when the composition of the aqueous phase has reached a point selected within the ranges for i), ii) and iii) of about 3 to 15% hydrogen peroxide, about 55 to 80% sulphuric acid, and the balance being at least about 10% water, with the consequence that the A value of the aqueous phase of the reaction mixture in step 3 remains substantially constant or increases as the carboxylic acid solution is introduced therein, the extent of the minimum increase in A value being inversely related to the carboxylic acid solubility;

4. Solid peroxyacid product produced during step 3 is separated from aqueous phase and retained as product.

Herein, for the purpose of determining how much of each of sulphuric acid, water and hydrogen peroxide is present in a composition, for example the Caro's acid solution, the figures given represent the respective amounts of the three components that would be present if the equilibration reaction did not take place. Thus, for example, the figure for sulphuric acid includes the proportion which in fact has been converted to peroxymonosulphuric acid as well as the proportion which remained unconverted, and similarly the figure for hydrogen peroxide includes the proportion which was also converted to peroxymonosulphuric acid.

By the use of the process according to the present invention, it is possible to obtain reaction between the carboxylic acid and the peroxidising species, i.e. hydrogen peroxide or H2SO5, without the carboxylic acid passing out of solution. This makes the process simpler and safer to control because it avoids the variable of the carboxylic acid being present as a separate phase from the aqueous phase in which the desired reaction takes place. The resultant peroxycarboxylic acid has been found to enjoy lower solubility than the carboxylic acid from which it has been formed in the prevailing aqueous composition, and consequently precipitates out of solution as it is formed.

As a result of so controlling the nature of the carboxylic acid feedstock, in conjunction with the composition of the Caro's acid phase, the inventors have been able to provide a process which needs only a comparatively low sulphuric acid content during at least a major proportion of the reaction time than has previously been suggested for a directly comparable batch process. The manner of addition of the carboxylic acid solution to the Caro's acid solution and the composition of the two reactants means that any change in the composition of the aqueous phase in the reaction is constantly towards instead of through hazardous compositions. Accordingly, the process can be easily halted, and indeed the process sequence is so designed that reagent addition terminates before a hazardous composition region is reached. Also, the manner of introduction of the carboxylic acid of the instant invention means that the total amount of dissolved organic compounds is kept at very low levels in the reaction mixture throughout the process when peroxidising species are present. This again acts as a feature promoting safe operation of the process.

Advantageously, the invention process also avoids the method of Parker et al which comprised the introduction of hydrogen peroxide solution into a carboxylic acid/sulphuric acid. The Parker method not only produces the rather small crystals according to its critic, Hutchins, but suffers far more seriously from the fact that the composition of the aqueous sulphuric acid phase inevitably passes into a region of extreme hazard in or around about 85/90% sulphuric acid content as a result of gradual addition of the hydrogen peroxide solution. It also maximises the amount of organic material that is present in the aqueous phase when a peroxidising species is present, which decreases safety during the operation of the process. Whilst Parker's method can just be contemplated on a laboratory scale behind suitably protective screens, it is absolutely impractical for commercial plant operation.

Accordingly, it will be recognised that the present invention process combines the advantages of operating with a preformed Caro's acid solution with the advantages of employing the carboxylic acid in a liquid form.

The invention process is applicable to the formation of peroxyacid from poorly water soluble aliphatic carboxylic acids. This term includes not only compounds that contain simply a linear or branched hydrocarbon structure that carries at least one carboxylic acid substituent, but additionally includes derivatives in which a further substituent, such as an aromatic group is sufficiently separated from the carboxylic acid substituent by the aliphatic hydrocarbon structure that it has no significant influence upon the peroxidation reaction, ie the starting material is accepted as essentially aliphatic in the vicinity of the reaction point. Accordingly, the invention process encompasses as starting material linear or branched aliphatic monocarboxylic acids containing from 8 to 12 carbon atoms, including nonanoic acid, iso-nonanoic acid, captic acid, and lauric acid, or mixtures of any two or more thereof. Alternatively, the starting material may comprise aliphatic dicarboxylic acids, often alpha,omega dicarboxylic acids containing from 6 to 16 carbon atoms, including suberic acid, azelaic acid, 1,10-decanedioic acid, 1,12-dodecanedioic acid, 1,14-tetradecanedioic acid and 1,16-hexadecanedioic acid.

In a third and potentially interesting variation, the starting material can comprise compounds of general formula R'-A-CO2H in which A represents a hydrocarbon diradical separating the substituent R' from the carboxylic acid carbon atom by at least 3 and often from 3 to 8 carbon atoms linearly, and R' represents a non-aliphatic substituent. R' can be an unsubstituted aromatic such as phenyl, or be substituted by a non-interfering substituent such as an alkyl or halo group, eg methyl, tertiary butyl, chloro or bromo or can comprise an aromatic amide or imide group, ie have one of the formulae:

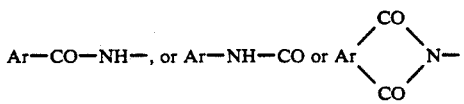

in which Ar preferably represents a phenyl group. It will be recognised that the phenyl group itself may be substituted by an alkyl group, such as containing up to 12 carbon atoms, and/or by a second amidoalkanoic acid or imidoalkanoic acid group. The process has particular applicability to phthalamidoalkanoic acids and phthalimidoalkanoic acids containing from 4 to 7 linear carbon atoms in the alkanoic acid group, such as phthalimidohexanoic acid, which hereinafter may be alternatively referred to as PICA for convenience.

Alternatively, in a fourth variation similar to variation 3, the starting material is also an amido or imidoalkanoic acid of formula R'-A-CO2H in which A represents a hydrocarbon diradical separating the substituent R' from the carboxylic acid carbon atom by at least 2 and often up to 8 carbon atoms linearly, and R' represents an aliphatic substituent satisfying the subformula:

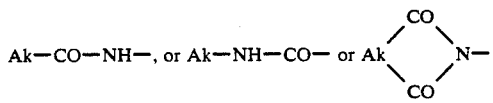

in which Ak represents an alkyl group containing at least 6 carbons or a dimethylene group, optionally alkyl substituted or forming part of a cycloaliphatic nucleus. Representative compounds include octanamido or nonanamidosuccinic acid succinimidobutyric acid or hexahydrophthalimidocaproic acid.

Within the broad ambit of the present invention, it will be recognised that there are a number of variables under the control of the process operator. These include, in particular, the composition of the carboxylic acid solution, the composition of the Caro's acid solution, the overall weight ratio of the two solutions employed and the temperature of the reaction mixture in step 3.

It must be understood that the inherent solubility of the carboxylic acid starting material is of considerable influence upon the selection of the operating values for the variables within the broad limits. As a general guideline, there is a preferred operating window of conditions for each starting material that is positioned in accordance with the inherent solubility of the carboxylic acid in aqueous sulphuric acid liquors. By way of general guidance, carboxylic acid starting materials which have solubility towards the upper end of the solubility range, such as PICA, tend to benefit from employing less stringent operating conditions than carboxylic acids which have a solubility towards the lower end of the solubility range such as dodecanedioic acid, sometimes referred to herein as DDA. In this context, the term "stringent" implies in particular the presence of a greater proportion of sulphuric acid in the solution in which the carboxylic acid is dissolved in step 1 or alternatively (or additionally) the use of a higher ratio of carboxylic acid solution produced in step 1 to the Caro's acid solution produced in step 2. The use of more stringent conditions results in the reaction mixture containing a higher sulphuric acid content than if less stringent conditions had been employed. In addition, more stringent conditions are preferably operated in conjunction with a higher operating temperature. The subsequent description of preferred embodiments should accordingly be read in the light of the foregoing generalisations.

The range of sulphuric acid concentrations that it is practical to employ depends upon which carboxylic acid is being employed. It is practical to use sulphuric acid of at least 90% strength and sometimes most convenient and preferable to employ sulphuric acid of at least 95% w/w as the solvent for carboxylic acids of similar solubility to DDA, ie carboxylic acids of inherently poorer solubility. It is also practical to employ such sulphuric acid concentrations for the slightly more soluble carboxylic acid reagents than DDA, but as the inherent solubility of the carboxylic acid increases, it becomes increasingly practical to select a lower strength sulphuric acid as solvent. Thus, for a compound like PICA, it is practical, from some points of view, to employ in step 1 a sulphuric acid concentration as low as around 80%.

The solutions can be made in step 1 readily by mixing the two components at a suitable temperature to promote the dissolution process, and preferably under enclosed conditions so as to prevent or minimise the loss or particles of carboxylic acid into the atmosphere. Either ambient or elevated temperature solutions can be produced, preferably not exceeding 60° C. It is particularly convenient for the solution after it has been made to have a temperature that does not exceed the temperature adopted in step 3, although to accelerate dissolution of the carboxylic acid, the sulphuric acid solvent may be heated during the dissolution and subsequently cooled or allowed to cool to the desired temperature for its introduction into the reaction mixture. It will be seen that the technique enables the process operator to avoid the use of finely ground solid particles advocated by Bettle in his above-identified U.S. patent specification, and thereby avoids the dust and hazard implications of Bettle's process. It will be further recognised that such beneficial conditions would be significantly more risky if the dissolution were to take place in the presence of peroxidising species, ie in a manner that is not according to the instant invention.

The composition of the Caro's acid solution made in step 2 is decided in conjunction with the composition of the sulphuric acid solvent for the carboxylic acid so that the total amount of sulphuric acid provided by both compositions is appropriate for the selected carboxylic acid starting material and peroxyacid product. Where the one composition provides a relatively high amount of sulphuric acid, then the other composition tends to provide a correspondingly low amount of sulphuric acid, but viewed in the light of the overall requirement of the starting carboxylic acid material.

One other and implicit factor taken into account when determining the actual concentration of sulphuric acid in the Caro's acid to provide the complementary amount is the overall volume of liquor in the reaction mixture at the end of introduction of the carboxylic acid solution in step 3 relative to the amount of percarboxylic acid solids. Where the ratio of the two is low, the concentration of sulphuric acid in the Caro's acid is also relatively low and vice versa in order to attain the same sulphuric acid concentration in the aqueous phase of the reaction mixture at the end of the introduction of the carboxylic acid solution. The resultant difference in the strength of the Caro's acid solution is naturally more pronounced when the highest strength sulphuric acid concentration is employed for dissolving the carboxylic acid.

The concentration of sulphuric acid in the Caro's acid solution is normally selected in the range of 5 to 70% w/w, is often at least 35% w/w and commonly in the range 40 to 65% w/w.

For the most poorly soluble starting materials like DDA or even higher weight dicarboxylic acids, it is desirable in some embodiments, though not essential to employ Caro's acid solutions towards the upper end of the range as regards its sulphuric acid content. By way of illustration, a concentration of around 55 to 65% w/w sulphuric acid is convenient, together with hydrogen peroxide content of preferably around 10 to 20%, especially 12 to 18% and water providing the residue. For the less poorly soluble carboxylic acid starting materials like PICA or alkylamidosuccinic acids, in other embodiments, it is often convenient to start with a composition containing somewhat lower amounts of sulphuric acid than indicated for DDA, such as an intermediate range of from 45 to 55% w/w or even 40-45% w/w, and a correspondingly higher amount of water, so that advantage can be taken of employing a relatively lower sulphuric acid concentration in the reaction mixture. The hydrogen peroxide content is chosen preferably within the range 10 to 20% and especially 12 to 18% w/w. Advantage can therefore be taken for compounds like PICA to be peroxidised under conditions even further from hazardous regions.

However, in yet other embodiments, it is possible to employ intermediate range strength Caro's acid solutions in conjunction with any of the carboxylic acids, provided that the total amount of sulphuric acid in the reaction mixture in step 3 is sufficiently high for the peroxycarboxylic acid to precipitate out. Such a process variation is preferably operated in conjunction with either an extended period of introduction of the carboxylic acid solution into the reaction mixture and/or an extended post-introduction or digestion phase. For use in conjunction with the more insoluble acids, the sulphuric acid concentration in the Caro's acid solution is usually at least 35% w/w. Progressively, the practical lower limit for sulphuric acid strength falls below 35% as the solubility of the carboxylic acid becomes higher.

For convenience herein, reference is made from time to time to the term "A value" of an aqueous composition by which is meant the fraction obtained by dividing the sulphuric acid weight therein, S, by the sum of the weight of sulphuric acid and water therein, $[S+W]$. An important factor in the invention process comprises the difference in strength of the sulphuric acid solutions used in steps 1 and 2, which can be expressed as the difference in A value ($^\wedge$A) between the two reagent solutions, A1-A2. The minimum and maximum difference in $^\wedge$EA value is respectively about 0 and 0.9. The practical breadth of the range that is useable varies in line with the solubility of the carboxylic acid being peroxidised. For carboxylic acids like dodecanedioic acid A1 normally exceeds A2 by at least 0.2, and is normally less than about 0.6, sometimes in the range 0.2 to 0.3 but sometimes also from 0.3 to about 0.5. As the solubility of the acid increases to or beyond that of PICA the practical range for $^\wedge$A broadens, the minimum $^\wedge$A for practical working reducing towards 0 and the maximum $^\wedge$A increasing towards 0.9

During step 2, the formation of Caro's acid is strongly exothermic, and accordingly, the composition is normally cooled by the provision of a cooling jacket or coils through which a cold fluid is pumped or by passage through a cooling heat exchanger. Conveniently, the cooling is so controlled as to produce a temperature at or similar to the process temperature of step 3. It will be recognised as a benefit of the instant process that a significant proportion of the heat inherent in conducting a peroxidation in a sulphuric acid/hydrogen peroxide reaction medium can be generated and removed prior to the organic compounds being present, thereby minimising the risks of a self-accelerating decomposition procedure being set in train, inadvertantly.

The temperature of the reaction mixture is preferably maintained within a sub-range of the broad range which varies inversely to the relative solubility of the carboxylic acid in aqueous sulphuric acid mixtures. As the relative solubility increases from the very poorly soluble, like DDA to the less poorly soluble, like PICA, the preferred reaction temperature decreases from the sub-range of 35° to 45° C. to the sub-range of 15° to 30° C. Maintenance of mixture in the preferred temperature sub-range assists in promoting an effective balance of crystal nucleation and growth of the selected peroxyacid, to attain a product which can be recovered more easily and a reaction mixture of reasonable viscosity.

One of the important aspects of the present process resides in step 3, namely controlling the rate of introduction of the carboxylic acid solution into the body of Caro's acid solution. Qualitatively, the rate is slow and progressive, by which latter term is meant that solution is introduced as a stream or in the form of extremely small increments which for practical purposes is in essence like a stream. The rate is controlled so as to prevent the carboxylic acid precipitating out when it encounters the body of Caro's acid solution. A suitable rate can naturally be established for each starting material under the prevailing conditions by small scale tests and prior observation of the solubility profile for the starting material. The most preferred rate from the viewpoint of maximising through-put is that which is virtually bordering upon the rate at which carboxylic acid would begin to precipitate out in any significant extent. It will be recognised of course that such a rate will be dependent upon the temperature, and the composition of the aqueous phase as well as the nature of the carboxylic acid composition that is introduced.

The rate of introduction of the carboxylic acid solution in step 3 may be kept constant during the entire introduction of the carboxylic acid, at its initial rate, but in a preferred variation the rate is increased as the reaction progresses. The increase tends to be least in the initial stages and accelerates towards the end of the reaction. Thus, when so operated, the rate tends to follow the change in sulphuric acid content of the aqueous phase. It will also be seen that the increase in addition rate tends to enable cooling equipment to be matched better to the plant capacity. Initially, the difference between the Caro's acid body of fluid and the carboxylic acid solution is at its greatest, so that the heat of dilution is at its greatest. Later on, when the difference in composition is smaller, so that the heat of dilution is correspondingly smaller per unit addition of carboxylic acid solution, the rate of introduction of the solution is greater so that there is a tendency to balance the two effects. This enables the process user to optimise the size of his cooling capacity.

A further advantage of the manner of introduction of the carboxylic acid manifests itself in the convenient rate of nucleation and smooth deposition of peroxyacid product, thereby forming especially under preferred core operating conditions a relatively large and readily filtered crystalline product The total period for introducing the carboxylic acid solution is often selected within the range of from 30 to 200 minutes, the preferred section of the range depending upon the solubility of the carboxylic acid under the prevailing conditions, the better the solubility, the shorter the permissible introduction period. As has been referred to hereinbefore, solubility increases with both increase in sulphuric acid content and increase in temperature. To some extent, at least, a relative decrease in inherent solubility can be compensated by an increase in reaction temperature. The period of introduction is often selected in the range of from 45 to 90 minutes at a preferred reaction mixture temperature in step 3 of from 15° to 30° C. for acids like PICA, and increased for acids like DDA, to a preferred reaction mixture temperature of from about 35° to 45° C. It is of course suitable to employ a slower rate of introduction of the carboxylic acid solution, such as selected in the range of 90 to 150 minutes, but at the expense of reduced through-put. From the product quality stand point, though, it is often at least as good as at the slightly faster rate of introduction.

Whilst the reaction process may be terminated as soon as all the carboxylic acid feedstock has been introduced, it is preferable to allow a further period in which the reaction can progress more fully to completion and if desired to allow some digestion of the crystalline product. This is particularly desirable if ˆA is in the region of at least 0.4. A convenient post-introduction period is often up to about 150 minutes and in some instances is from 10 to 60 minutes In other instances when ˆA was high, it can conveniently comprise 60 to 120 minutes. Thus, a convenient combined period for a starting material like PICA comprises about 80 to 100 minutes at around ambient temperature reaction, though it may sometimes last from 100 to about 150 minutes.

The total amount of carboxylic acid solution to be introduced per unit volume of Caro's acid solution will depend, of course, upon the actual composition of each, and especially upon the concentration of carboxylic acid in the sulphuric acid solvent. In many instances the carboxylic acid concentration will be chosen within the range of from 20 to 40% w/w, depending upon the solubility of the material and the viscosity of the resultant solution. At the lower end of the carboxylic acid concentrations, eg 20 to 25% solutions, the carboxylic acid solution: Caro's acid weight ratio will be commonly selected within the range of from 1.5:1 to 1:1.7. This can be particular suitable for acids like PICA. As the carboxylic acid concentration increases, the ratio tilts in favour of more Caro's acid, towards the ratio range of from 1:1.8 to about 1:2.5 at a carboxylic acid concentration of about 35%. The overall range span is therefore normally from 1.5:1 to 1:2.5. In many embodiments roughly half, say 40 to 60% of the total sulphuric acid is introduced as solvent for the carboxylic acid and the balance in the Caro's acid solution. In some other embodiments in which ˆA is high, the proportion of sulphuric acid in the carboxylic acid solution is rather higher, and in the range of 60 to 75%. Either way, in view of the concentration of hydrogen peroxide in the Caro's acid solution preferably comprising at least 10% w/w, it means that the amount of hydrogen peroxide employed is normally significantly in excess of the stoichiometric amount.

The aqueous phase of the reaction mixture normally contains a higher weight fraction and in many embodiments a substantially higher weight fraction of sulphuric acid at the end compared with the start of step 3, depending upon ˆA. Whilst it would be feasible, in those embodiments in which there is a significant increase in sulphuric acid fraction, to choose to operate by introducing the carboxylic acid solution until a predecided maximum sulphuric acid content is attained, the actual point being selected in the light of the solubility of the carboxylic acid and the percarboxylic acid, it is often more convenient to prepare in steps 1 and 2 the appropriate amounts of the two solutions so as to attain that sulphuric acid content when they are fully mixed together.

The target proportions of sulphuric acid and water in the aqueous phase of the reaction mixture at the end of the reaction period are chosen normally in the light of the solubility characteristics of the carboxylic acid reactant and peroxycarboxylic product and normally within the ranges of about 55 to 80% w/w sulphuric acid and about 10 to 40% water. For a product like phthalimidoperoxyhexanoic acid, the final sulphuric acid content is often selected in the range of about 60 to 67% w/w in the aqueous phase and in addition, which corresponds to an A value that is often from 0.7 to 0.75. For the production of relatively soluble peroxyacids, such as p-chloroperoxyadipanilic acid, it can be convenient for the final sulphuric acid content to likewise fall in the range of 60–67% w/w but advantageously, it can fall below 60% w/w, such as from about 55 to 60% w/w and the selected final A value would accordingly be less than 0.7, such as from 0.6 to 0.7.

For less soluble peroxyacids, such diperoxydodecanedioic acid the preferred range of A value in the reaction mixture at the end of step 3 tends to overlap at its lower end with the upper end of the range for more soluble peroxyacids, from about 0.72 to about 0.8 and especially up to about 0.76. This means a correspondingly higher preferred range of residual proportions of sulphuric acid in the reaction mixture, approximating to about 65 to 75% w/w, and a corresponding content of water towards the lower end of its range, such as from 10 to 25%. The A value changes by virtue of the introduction of the higher strength sulphuric acid in the carboxylic acid solution. This could, if desired, be augmented by a separate addition of concentrated sulphuric acid, or by diluting the carboxylic acid solution with extra sulphuric acid.

The reaction in step 3 can be carried out in the presence of additional solids material, which in practice is normally an extra amount of the peroxyacid, such as produced in a previous batch. The amount of such additional solids is often selected in the range of from 0 to 10% w/w based upon the weight of the reaction mixture. Its presence can promote a larger average particle size for the product.

The reaction can be carried out in conventional reaction vessels or tanks equipped with means to thoroughly agitate the mixture, preferably avoiding excessive shear so as to minimise fragmentation of the product crystals. The vessels and pipework should preferably be made from materials that are resistant to corrosion from aqueous sulphuric acid solutions, such as from appropriate grades of steel or be lined with a suitably resistant elastomeric lining.

The particulate peroxyacid product is separated from the aqueous phase at the end of the reaction. Conventional solid/liquid separating devices can be used, including filters or centrifuges. By virtue of the way in which the product is made, we have found that it has only a low residual carboxylic acid content. Thus, in many instances, not only is the product rather pure, but a high conversion to the percarboxylic acid is achieved.

The solid phase is retained as the product, and usually contains a substantial weight of aqueous phase. Since sulphuric acid impurity tends to impair the stability of peroxycarboxylic acids, it is preferable to water-wash and dry the product. Alternatively, or additionally, and depending upon the inherent safety of the peroxyacid, it can be desirable to effect desensitisation of the peroxyacid before it is allowed to dry out. This can be effected by known techniques, such as the in situ partial neutralisation of the entrained sulphuric acid with a suitable alkali such as a sodium or magnesium hydroxide and/or by mixing the damp product with a desensitiser such a boric acid or sodium or magnesium sulphate that is prepared beforehand. Such desensitisation is particularly desirable for the diperoxyalkanoic acids like DPDDA, but can often be unnecessary for the much safer compounds like phthalimidoperoxyhexanoic acid or phthaliamidoperoxyhexanoic acid.

The mother liquor contains a significant content of hydrogen peroxide/permonosulphuric acid. In order to improve the economics of the process, the mother liquor can be recycled at least in part after its composition has been adjusted to approximately that of the Caro's acid solution produced in step 2. Such adjustment is made by diluting the mother liquor with water to reduce the A value and concentrated hydrogen peroxide solution to increase the residual hydrogen peroxide level. The dilutions can be sequential or simultaneous. In practice, it is often not possible to recycle the entire volume of mother liquor because the retained amount of liquor in general and sulphuric acid in particular is too great. In such circumstances, the loss of a fraction of the mother liquor acts as a means to remove byproducts from the reaction, and in particular degradation products of the carboxylic acid and thereby reduce the rate at which they would build-up during multiple recycle of the mother liquor. Periodically, the entire batch of mother liquor can be discarded, if desired.

If desired, the mother liquor can be diluted with an aqueous medium, such as water itself or aqueous hydrogen peroxide solution, such as enough for recycling or an excess amount. The net result of dilution is to reduce the solubility of the peroxyacid product, and thereby cause a further amount of precipitate to form, which can subsequently be recovered. An alternative or additional means for reducing the peroxyacid solubility comprises cooling the liquor, preferably to below about 10° C. or by at least 10° C. below the reaction temperature of step 3. Both procedures minimise the amount of carboxylic acid and peroxyacid product that is recycled, so that the extent of their degradation is also minimised. By reducing the residual content of organic species in solution, recycling the mother liquor is rendered a less hazardous procedure.

The peroxycarboxylic acids produced by a process according to the instant invention can be employed for the various known uses for such compounds, including incorporation in fabric bleaching or washing compositions, and especially those intended for operation at hand hot temperatures or lower, in disinfectant or sanitizing compositions for solid surfaces, liquid media or gasses, or as a reagent for oxidising reactions or for polymerisation or cross linking ethylenically unsaturated materials.

Having described the invention in general terms, certain embodiments thereof will now be described more fully by way of example only.

EXAMPLE 1

Phthalimidohexanoic acid, 30 g, was dissolved in sulphuric acid solution, 80% w/w, 90 g, at 20° C. A Caro's acid solution was prepared by mixing with cooling to about 20° C. water, concentrated hydrogen peroxide and concentrated sulphuric acid to provide 90g of a solution containing 50% w/w sulphuric acid, 20% w/w hydrogen peroxide and 30% w/w water, which is equivalent to an A value of 0.625.

The solution of phthalimidohexanoic acid was then introduced into Caro's acid solution at a rate of 2 g per minute with constant stirring and cooling to 20° C. The introduction was complete after 1 hour, and the reaction mixture, which had the form of a thick slurry, was stirred for a further 30 minutes. The mixture was filtered and the solids washed with three portions, each of about 200 ml of demineralised water, yielding 26.1 g of a white crystalline product which analysis confirmed as phthalimidoperoxyhexanoic acid at a purity of 96%. The mother liquor was retained for recycle.

EXAMPLE 2

Phthalimidohexanoic acid, 30 g, was dissolved in sulphuric acid solution, 98% w/w, 40.5 g, at 20° C. A Caro's acid solution was prepared by mixing with cooling to about 20° C. water, concentrated hydrogen peroxide and concentrated sulphuric acid to provide 130.5 g of a solution containing 50% w/w sulphuric acid, 20% w/w hydrogen peroxide and 30% w/w water, which is equivalent to an A value of 0.625.

The solution of phthalimidohexanoic acid was then introduced into Caro's acid solution at a rate of 1.18 g per minute with constant stirring and cooling to 20° C. The introduction was complete after 1 hour, and the reaction mixture, which had the form of a thick slurry, was cooled to 10° C. and stirred for a further 1 hour. The mixture was filtered and the solids washed with three portions, each of about 200 ml of demineralised water, yielding 23.8 g of a white crystalline product which analysis confirmed as phthalimidoperoxy-hexanoic acid at a purity of 99.9%. The mother liquor was retained for recycle.

EXAMPLE 3

In Example 3, dodecanedioic acid, 50 g, was dissolved in sulphuric acid solution, 96.4% w/w, 116.7 g, at 20° C. A Caro's acid solution, 378.25 g, containing 253.4 g H2SO4, 39.7 g H2O2 and 85.1 g H2O (A value 0.749) was prepared by mixing concentrated sulphuric acid, water and concentrated hydrogen peroxide with cooling to 45° C.

The dodecanedioic acid solution was introduced with stirring into the Caro's acid solution continuously at a rate of 2.78 g per minute for a period of 1 hour, the reaction being maintained at 45° C. The mixture was stirred for a further 30 minutes at the same temperature, filtered and the solids washed with water. The resultant product, 55g, had a purity of 95.3% diperoxydodecanedioic acid.

Example 3 was repeated, (Example 3A) but employing a Caro's acid solution which contained 221.2 g H2SO4, 51.7 g H2O2 and 105.3 g H2O, (A value 0.677). Substantially the same recovery and purity was obtained.

Example 3A, which is preferred, demonstrates that product quality can be maintained by following the instant process, whilst reducing the A value of the reagent and the reaction mixture, so that at no time, even at the end of the reaction when all the sulphuric acid has been added does the mixture an unsafe or meta-safe composition.

EXAMPLE 4

In Example 4, lauric acid, 20 g, was dissolved in concentrated sulphuric acid solution, 98.0% w/w, 60 g at ambient temperature. A Caro's acid solution, 60 g, containing 37% w/w H2SO4, 20% w/w H2O2 and 43% w/w H2O (A value 0.463) was prepared by mixing concentrated sulphuric acid, water and concentrated hydrogen peroxide with cooling to about 20° C.

The lauric acid solution was introduced with stirring into the Caro's acid solution continuously at a rate of 1.6 g per minute for a period of 50 minutes, the reaction mixture being maintained at 35°–40° C. At the end of the addition the solution was clear. The mixture was stirred for a further 2 hours at about 40° C., during which period a crystalline product precipitated. Solids were recovered from the mixture by the following method, hereinafter SRT for short, in which a)the mixture was cooled to about 10° C., b) quenched by mixture with an approximately equal volume of ice/water, the solid product was washed with water until the filtrate had a pH of about pH5 and air dried. The yield was 24g, having a purity of 71.3% peroxylauric acid.

EXAMPLE 5

In Example 5, nonanoic acid, 20 g, was dissolved in concentrated sulphuric acid solution, 98.0% w/w, 60 g at ambient temperature. A Caro's acid solution, 60 g, containing 37% w/w H2SO4, 20% w/w H2O2 and 43% w/w H2O (A value 0.463) was prepared by mixing concentrated sulphuric acid, water and concentrated hydrogen peroxide with cooling to about 20° C.

The carboxylic acid solution was introduced with stirring into the Caro's acid solution continuously at a rate of 2.67 g per minute for a period of 30 minutes, the reaction being maintained at 25°–30° C. The mixture was stirred for a further 1.5 hours at 30° C., and subjected to SRT. The resultant product, 25.7 g, had a purity of 76.2% pernonanoic acid.

EXAMPLE 6

In Example 6, phthalimidobutyric acid, 20 g, was dissolved in concentrated sulphuric acid solution, 98.0% w/w, 60 g at ambient temperature. A Caro's acid solution, 60 g, containing 37% w/w H2SO4, 20% w/w H2O2 and 43% w/w H2O (A value 0.463) was prepared by mixing concentrated sulphuric acid, water and concentrated hydrogen peroxide with cooling to about 20° C.

The carboxylic acid solution was introduced with stirring into the Caro's acid solution continuously at a rate of 2.67 g per minute for a period of 30 minutes, the reaction being maintained at 20° C. The mixture was stirred for a further 90 minutes at the same temperature, and solids recovered by the SRT method. The resultant product, 18.5 g, had a purity of 94.3% phthalimdoperoxybutyric acid.

EXAMPLE 7

In Example 7, p-chloroadipanilic acid, 20 g, was dissolved in concentrated sulphuric acid solution, 98.0% w/w, 60 g at ambient temperature. A Caro's acid solution, 60 g, containing 6% w/w H2SO4, 26.6% w/w H2O2 and 67.4% w/w H2O (A value 0.082) was prepared by mixing concentrated sulphuric acid, water and concentrated hydrogen peroxide with cooling to ambient temperature.

The carboxylic acid solution was introduced with stirring into the Caro's acid solution continuously at a rate of 2.67 g per minute for a period of 30 minutes, the reaction being maintained at 20° C. The mixture was stirred for a further 2 hours at the same temperature, and subjected to the SRT method. The resultant product, 20.1 g had a purity of 91.0% chloroperoxyadipanilic acid.

EXAMPLE 8

In Example 8, 6,6'-terephthal-di(amidohexanoic) acid, 20 g, was dissolved in concentrated sulphuric acid solution, 98.0% w/w, 80 g at ambient temperature. A Caro's acid solution, 83.5 g, containing 37.4% w/w H2SO4, 20.8% w/w H2O2 and 41.8% w/w H2O (A value 0.472) was prepared by mixing concentrated sulphuric acid, water and concentrated hydrogen peroxide with cooling to ambient temperature.

The carboxylic acid solution was introduced with stirring into the Caro's acid solution continuously at a rate of 3.33g per minute for a period of 30 minutes, the reaction being maintained at 20°–25° C. The mixture was stirred for a further 2 hours minutes at 30° C., and subjected to the SRT method. The resultant product, 19.9 g, had a purity of 89.0% 6,6'-terephthal-di(amidoperoxyhexanoic) acid

EXAMPLE 9

In Example 9, 6,6'-fumaryl bis(amidohexanoic) acid, 20 g, was dissolved in concentrated sulphuric acid solution, 98.0% w/w, 80 g at ambient temperature. A Caro's acid solution, 80 g, containing 39% w/w H2SO4, 17.3% w/w H2O2 and 43.7 w/w H2O (A value 0.472) was prepared by mixing concentrated sulphuric acid, water and concentrated hydrogen peroxide with cooling to ambient.

The carboxylic acid solution was introduced with stirring into the Caro's acid solution continuously at a rate of 3.33 g per minute for a period of 30 minutes, the reaction being maintained at 30° C. The mixture was stirred for a further 2 hours at 40° C. and then subjected to SRT. The resultant product, 16.9 g had a purity of 70% 6,6'-fumaryl bisamidoperoxyhexanoic acid.

EXAMPLE 10

In Example 10, nonanamidosuccinic acid, 15 g, was dissolved in concentrated sulphuric acid solution, 98.0% w/w, 45 g at ambient temperature. A Caro's acid solution, 45 g, containing 30% w/w H2SO4, 30% w/w H2O2 and 40% w/w H2O (A value 0.423) was prepared by mixing concentrated sulphuric acid, water and concentrated hydrogen peroxide with cooling to ambient temperature.

The carboxylic acid solution was introduced with stirring into the Caro's acid solution continuously at a rate of 3g per minute for a period of 20 minutes, the reaction being maintained at 20°–25° C. The mixture was stirred for a further 1 hour at the same temperature, and then subjected to the SRT. The resultant product, had a purity of 86.0% nonanamidoperoxysuccinic acid.

I claim:

1. 6,6'-terephthal-di(amidoperoxyhexanoic) acid.

* * * * *